US011618765B2

(12) United States Patent
Kalman

(10) Patent No.: US 11,618,765 B2
(45) Date of Patent: Apr. 4, 2023

(54) BROAD-SPECTRUM ANTIVIRAL NUCLEOSIDE DERIVATIVES

(71) Applicant: Thomas I. Kalman, East Amherst, NY (US)

(72) Inventor: Thomas I. Kalman, East Amherst, NY (US)

(*) Notice: Subject to any disclaimer, the term of this patent is extended or adjusted under 35 U.S.C. 154(b) by 0 days.

(21) Appl. No.: 17/325,443

(22) Filed: May 20, 2021

(65) Prior Publication Data
US 2021/0363169 A1  Nov. 25, 2021

Related U.S. Application Data

(60) Provisional application No. 63/028,100, filed on May 21, 2020.

(51) Int. Cl.
*C07H 19/052* (2006.01)
*A61K 45/06* (2006.01)
*A61P 31/12* (2006.01)
*A61P 31/22* (2006.01)

(52) U.S. Cl.
CPC ......... *C07H 19/052* (2013.01); *A61K 45/06* (2013.01); *A61P 31/12* (2018.01); *A61P 31/22* (2018.01)

(58) Field of Classification Search
None
See application file for complete search history.

(56) References Cited

FOREIGN PATENT DOCUMENTS

| JP | 61171497 A | 8/1986 | |
|---|---|---|---|
| JP | 5432469 B2 | 3/2014 | |
| JP | 5432494 B2 | 3/2014 | |
| WO | 199421658 A1 | 9/1994 | |
| WO | WO/199421658 * | 9/1994 | ........... C07H 15/052 |

OTHER PUBLICATIONS

UNAIDS Data 2019, UNAIDS.org.
Jordheim, LP et al. Advances in the development of nucleoside and nucleotide analogues for cancer and viral diseases. Nature Rev. Drug Discovery, 2013, 12, 447.
Li, G and De Clercq, E, Therapeutic options for the 2019 novel coronavirus (2019-nCoV) Nat. Rev. Drug Discovery 2020, 19, 149.
Loeb, LA et al., Lethal mutagenesis of HIV with mutagenic nucleoside analogs. Proc. Natl. Acad. Sci. 1999, 96, 1492.
Kalman, T.I., Ed., Drug action and design: mechanism-based enzyme inhibitors. Developments in Biochemistry, vol. 6. Elsevier/North Holland, New York, 1979.
Mathur, P et al., Use of ribavirin for hepatitis C. treatment in the modern direct-acting antiviral era. J. Clin. Trans. Hepatol. 2018, 6, 431.
NIH.gov/coronavirus, ClinicalTrials.gov 2020, NCT04276688.
Ferron, F et al., Structural and molecular basis of mismatch correction and ribavirin excision from coronavirus RNA. Proc. Natl. Acad. Sci. 2018, 115, E162.
Stockman, JL et al., SARS: systematic review of treatment effects. Plos Med. 2006, 3, e343.
ClinicalTrials.gov, NCT04359615 2020.
NIH.gov/coronavirus, ClinicalTrials.gov, NCT04280705 2020.
Sheahan, TP et al., Broad-spectrum antiviral GS-5734 inhibits both epidemic and zoonotic coronaviruses. Sci. Transl. Med. 2017, 9, eaal3653.
Stuyver LJ et al., Ribonucleoside analogue that blocks replication of bovine viral diarrhea and hepatitis C viruses in culture. Antimicrob. Agents Chemother. 2003, 47, 244.
Sheahan, TP et al., An orally bioavailable broad-spectrum antiviral inhibits SARS-CoV-2 in human airway epithelial cell cultures and multiple coronaviruses in mice. Sci. Transl. Med. 2020, 12, eabb5883Sci. Transl. Med. 2020, 12, eabb5883.
Hernandez-Santiago, BI et al., Metabolism of the anti-hepatitis C virus nucleoside ?-D-N4-hydroxycytidine in different liver cells. Antimicrob. Agents Chemother. 2004, 48, 4636.
Jiang, X-J and Kalman, TI, Synthesis of a novel antiretroviral agent: 1-(2-deoxy-?-D-ribofuranosyl)-4-acetylimidazolin-2-one (imidine). Nucleosides Nucleotides 1994, 13, 379.
Kalman, TI et al., Mechanism of inhibition of HIV reverse transcriptase by 1-(2'-deoxy-?-D-ribofuranosyl)-4-acetylimidazolin-2-one (imidine). Nucleosides Nucleotides 1999, 18, 847.
Ikeda, H et al., The effects of two antipodal fluorene-induced sugar puckers on the conformation and stability of the Dickerson-Drew dodecamer duplex [d(CGCGAATTCGCG)]2. Nucleic Acid Res. 1998, 26, 2237.
Williams, AA et al., Impact of sugar pucker on base pair and mispair stability, Biochemistry 2009, 48, 11994.
Slater, MJ et al., Enzymatic synthesis and antiviral activity of 2'-deoxy-2'-fluoro-ribavirin. Bioorg. Med. Chem. Let. 1996, 6, 2187.
Perilkova et al., Synthesis of 2'-deoxy-2'-fluororibo- and 2'-deoxy-2',2'-difluororibonucleosides derived from 6-(het)aryl-7-deazapurines, Tetrahedron 2012, 68, 8300.
Shi, J. et al., Synthesis and antiviral activity of a series of D- and L-2'-deoxy-2'-fluororibonucleosides in the subgenomic HCV replicon system, Bioorg. Med. Chem. 2005, 13, 1641.
Cadena-Amaro, C and Pochet, S, Efficient incorporation of 1-(2-deoxy-?-D-ribofuranosyl)-2-oxo-imidazole-4-carboxamide, Tetrahedron 2005, 61, 5081.
Eigen, M, Error catastrophe and antiviral strategy. Proc. Natl. Acad. Sci. 2002, 99, 13374.
Doerr, IL and Fox JJ, 2'-Deoxy-2'-fluorocytidine, 1-?-D-arabinofuranosyl-2-aminofuranosyl-2-amino-1,4(2H-4-iminopyrimidine) and related derivatives. J. Org Chem. 1967, 32, 1462.

(Continued)

*Primary Examiner* — Traviss C McIntosh, III
(74) *Attorney, Agent, or Firm* — ArentFox Schiff LLP

(57) ABSTRACT

The disclosure relates to broad spectrum, direct acting antiviral agents. Disclosed is a group of novel nucleoside and nucleotide analogs having a 4-substituted imidazol-2-one heterocycle in place of the pyrimidine base of natural nucleic acid components and their prodrug derivatives (see Formula I).

18 Claims, 4 Drawing Sheets

(56) References Cited

OTHER PUBLICATIONS

Stuyver, LJ et al., Inhibition of subgenomic hepatitis C virus replicon in Huh-7 cells by 2'-deoxy-2'-fluorocytidine. Antimicrob. Agents Chemother. 2004, 48, 651.

Wagner, C et al., Pronucleotides: Toward the in vivo delivery of antiviral and anticancer nucleotides. Med. Chem. Rev. 2000, 20, 417.

Otter, BA, et al., Nucleosides. LXI. Transformations of pyrimidine nucleosides in alkaline media. IV. Conversion of 5-hydroxyuridines into imidazoline nucleosides. J. Org. Chem. 1969, 34, 2626.

Sanghani, SP, Human carboxylesterases: An update on CES1, CES2 and CES3. Protein Peptide Let. 2009, 16, 1207.

H. Kamiya et al., Recognition of Nucleotide Analogs Containing the 7,8-Dihydro-8-oxo Structure by the Human MTH1 Protein, J. Biochem. 140, 843-849 (2006).

T. Fukuda et al., An Alternative to the Mixed Probe Method in DNA Hybridization: Synthetic "lure" Nucleotide for the Ambiguous Position of Codons, 1986, Section B, a journal of chemical sciences.

P. C. Srivastava et al., Nucleosides of 4-Substituted Imidazoles, J. Org. Chem., vol. 40, No. 20, 1975.

H. Tanaka et al., Synthesis and Optical Properties of 2,5'-0-Cycloimidazole Nucleosides and Related Compounds (Nucleosides and Nucleotides. XXV1), Chem Pharm. Bull. 26, 3322-3329 (1978).

\* cited by examiner

BROAD-SPECTRUM ANTIVIRAL NUCLEOSIDE DERIVATIVES

CROSS-REFERENCE TO RELATED APPLICATIONS

The present application claims priority to and the benefit of the filing date of U.S. provisional patent application No. 63/028,100, filed on May 21, 2020, the contents of which are incorporated herein by reference in their entirety.

TECHNICAL FIELD

The disclosure relates to nucleoside derivatives and their use for the prevention and treatment of viral infections.

BACKGROUND

Failures to contain the COVID-19 global pandemic, caused by the RNA virus SARS-CoV-2, have illuminated the dire consequences of not having broad-spectrum antiviral drugs at hand having a high probability to be active against an emerging new virus. Beyond COVID-19, novel pathogenic viruses will continue to emerge. As one of the many requirements of an effective preparedness for such an occasion, broad-spectrum antivirals are needed for testing and rapid production and distribution. An additional reason for the need to develop and produce a ready supply of broad-spectrum antivirals is the inevitable emergence of drug resistance under the selective pressure exerted by any effective drug. Despite the rapid drug development and the effectiveness of multi-drug cocktails used in the treatment of AIDS, there were still about 38 million people living with AIDS and 940,000 died from AIDS-related illnesses globally in 2019 [1], three decades after the approval by the FDA of the first direct-acting anti-HIV drug, AZT.

SUMMARY

Nucleoside analogs have the potential to interfere with the replication of viral nucleic acids, resulting in the treatment of viral infections [2]. Previously developed antiviral nucleoside analogs may have the potential for repurposing to treat COVID-19 infections [3].

Nucleoside analogs are structurally related, but not identical to, the nucleosides normally used by mammalian cells and microorganisms to synthesize DNA and RNA. There are several ways nucleoside analogs may inhibit viral DNA and RNA synthesis. Their triphosphates may competitively inhibit viral DNA and RNA polymerases by competing with the natural nucleoside triphosphate substrates at the active sites of these enzymes and serve as substrates for the viral polymerases and incorporate into viral nucleic acids. Such incorporation may result in chain termination or lethal mutagenesis, which would prevent the replication of the viral genomes and the reproduction of infectious viral particles. Lethal mutagenesis scrambles the genetic codes of the viral genome, inactivating it [4]. In this respect, the analog triphosphates are "suicide substrates" or mechanism-based enzyme inhibitors [5], which instead of inactivating their target enzyme, inactivate the nucleic acid products of the enzyme-catalyzed reaction.

Ideally, antiviral nucleoside analogs should not adversely affect cellular nucleic acid synthesis to any significant extent. The analogs should be highly selective and lack toxic side effects.

Ribavirin is an example of a broad-spectrum antiviral nucleoside analog and has been used primarily for the treatment of hepatitis C infections, mostly in combination with pegylated interferon [6]. The structure of ribavirin closely resembles purine nucleosides, having a monocyclic triazole-carboxamide (a "truncated" purine) linked to the ribose sugar, instead of the bicyclic purine ring. The structure of ribavirin closely resembles purine nucleosides, having a monocyclic triazole-carboxamide (a "truncated" purine) linked to the ribose sugar, instead of the bicyclic purine ring. Ribavirin may exist in two interchangeable conformations, one resembling guanosine and the other, adenosine. The triphosphate metabolite of ribavirin can serve as a substrate for viral RNA-dependent RNA polymerase (RdRp), competing with GTP and ATP. Misincorporation of ribavirin monophosphate into viral RNA can cause mispairing that can interfere with the replication of the viral RNA.

Ribavirin is undergoing clinical trials for the treatment of COVID-19 [7]. However, it is not an ideal candidate, as it has serious side-effects, including hemolytic anemia, with potentially fatal outcome, particularly for patients with underlying heart conditions. Coronaviruses, such as SARS (SARS-CoV1), have mismatch repair capabilities, i.e., they can correct for replication errors by exonuclease cleavage of mismatched nucleotides at the 3'-end of the newly synthesized viral RNA, including ribavirin-5'-phosphate [8]. Indeed, ribavirin had poor efficacy in SARS patients and serious side effects [9].

Favipiravir (Avigan, T-705) is another antiviral. It is a truncated purine base analog that was approved in Japan for stockpiling against influenza pandemics in 2014. It is scheduled for clinical trials for treatment of hospitalized COVID-19 patients [10]. It has a mechanism of action like that of ribavirin, but a distinct metabolic activation to the ribosyl monophosphate by hypoxanthine-guanine phosphoribosyl transferase.

Remdesivir (GS-5734), an adenosine derivative, is another antiviral that inhibits the replication of several RNA viruses by a chain termination mechanism is. It has also been undergoing clinical trials for the treatment of COVID-19 [11] and was found to shorten the duration of hospitalization of Covid-19 patients. It received emergency use authorization from the FDA. Remdesivir was developed as a drug to treat Ebola infections and showed promising activities against MERS and SARS [12]. Its synthesis is complex, involving two intermediates requiring chiral resolution. Further, there are major shortcomings for world-wide applications of remdesivir treatment that include the following: 1) it must be administered by infusion, 2) its large-scale manufacturing and distribution at global proportions may not be feasible, and 3) it may not become universally available at affordable prices.

Ribavirin, flavipiravir, and remdesivir are purine derivatives, and their metabolically active form is their triphosphate nucleotide, which must compete with ATP and GTP for binding to their target protein, RNA-dependent RNA polymerase (RdRp). Since ATP may reach millimolar concentrations in cells, the dose of these drugs must be high enough to effectively compete with ATP (and GTP) to allow their incorporation into the viral RNA to a significant extent. However, the higher the dose, the more undesirable side effects may be produced by these drugs in vivo.

It is desirable to synthesize direct acting antivirals that are pyrimidine, rather than purine nucleoside analogs. An example of a pyrimidine nucleoside derivative that was previously developed as an anti-HCV agent is $N^4$-hydroxycytidine [13]. It was recently shown to be a broad-spectrum antiviral [14]. The IND of a prodrug of $N^4$-hydroxycytidine, EIDD-2801, recently received approval by the FDA. However, $N^4$-hydroxycytidine and its prodrugs are rapidly metabolized to both uridine and cytidine, which compete with the incorporation of the analog into RNA at the triphosphate level. In addition, it was concluded that the rapid degradation prevents its sufficient accumulation in target tissues to be able to exert its pharmacological activity [15].

Another example of a pyrimidine nucleoside analog as a direct acting antiviral is imidine (dImd), a thymidine analog [16], [17]. Imidine has shown selective anti-HIV activity with no cytotoxicity. For example, the $IC_{50}$ of the triphosphate of imidine (dImdTP) for inhibition of HIV-reverse transcriptase and Molt-4 DNA polymerase a, was 0.038 microM and 17 microM, respectively, showing a >400-fold selectivity. Its monophosphate (dIMP) readily incorporated into proviral DNA in place of dTMP, preferentially opposite to adenine (A) in the viral RNA template and caused a decrease in the fidelity of replication at the incorporated sites, due to misincorporation [18]. Imidine was less inhibitory to the growth of human cells in culture than thymidine, a natural component of DNA; an $IC_{50}$-value for imidine could not be reached at as high as 1000 micromolar concentration.

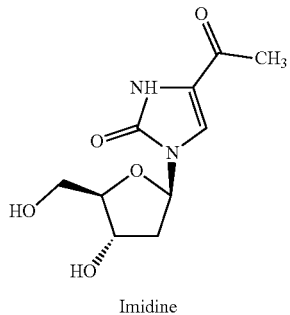 [SMILES: CC(=O)c1cn([C@H]2C[C@H](O)[C@@H](CO)O2)c(=O)[nH]1]

Imidine

There remains an unmet need for broad spectrum, direct acting antivirals that have the potential to show selective activity against a wide variety of pathogenic DNA and RNA viruses and have low toxicity. Thus, the present disclosure addresses this need and provides novel nucleoside and nucleotide analogs and their prodrug derivatives having a 4-substituted imidazol-2-one heterocycle in place of the pyrimidine base of natural nucleic acid components, and a fluorine substitution at the 2'-position of the sugar (Formula I):

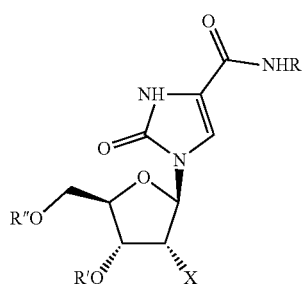

Formula I where X is H or F; R is H, or a linear or $C_{(1-7)}$ alkyloxycarbonyl group; R' is H, or a hydroxyl protecting group, e.g., an acyl, such as acetyl, butanoyl, benzoyl or amino acyl, such as valyl; R" is H, a hydroxy protecting group, e.g., an acyl, such as acetyl, butanoyl, benzoyl or amino acyl, such as valyl; or a phosphate ester, e.g., a 5'-monophosphate, 3',5'-cyclic phosphate, 5'-diphosphate and 5'-triphosphate, or an amino acid alkyl ester phosphoramidate PO(OPh)NHCR'''COOR'''' or phosphorodiamidate PO(NHCR'''COOR'''')$_2$, where R''' is an amino acid side chain and R'''' is a linear or branched $C_{(1-4)}$ alkyl.

Compounds of Formula I of the present disclosure provide pyrimidine nucleoside derivatives that can serve as broad-spectrum, direct acting antiviral drug candidates. The derivatives are prepared by synthetic procedures as described herein.

The compounds are broad-spectrum antiviral agents for potential use against SARS-CoV-2 and its drug-resistant mutants, as well as against other present and newly emerging pathogenic DNA and RNA viruses.

BRIEF DESCRIPTION OF THE DRAWINGS/FIGURES

Further advantages, features and details of the disclosure may be derived from the exemplary embodiments described below and with reference to the drawings. Example embodiments of the present disclosure are described in detail below with reference to the accompanying drawings to give those skilled in the art a clearer understanding of the abovementioned and other features and advantages of the present disclosure.

DETAILED DESCRIPTION

Figure 1:
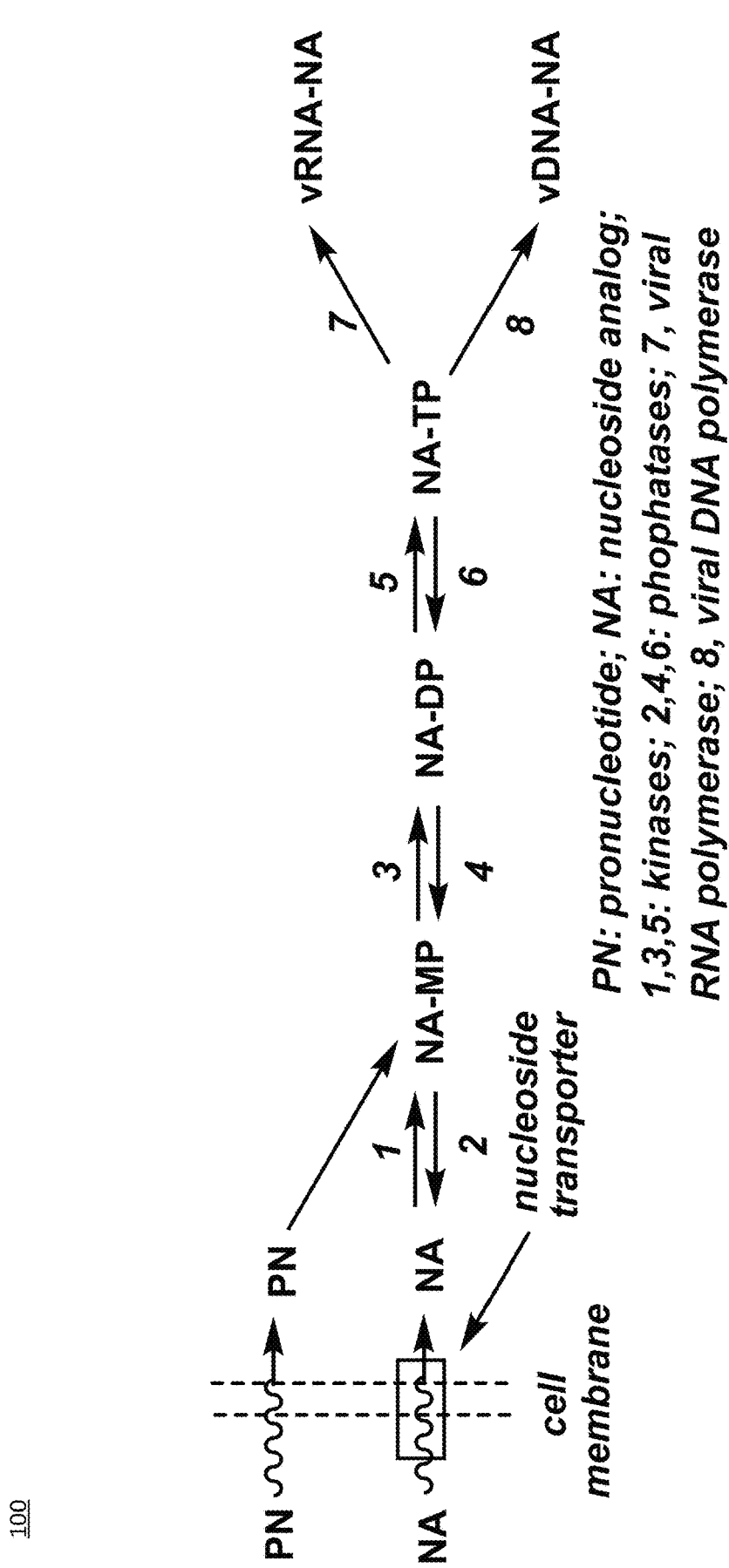
FIG. 1 shows an example outlining an intracellular metabolism of compounds of Formula I, in accordance with one or more embodiments of the present disclosure.

The present disclosure provides novel nucleoside and nucleotide analogs and their prodrug derivatives having a 4-substituted imidazol-2-one heterocycle in place of the pyrimidine base of natural nucleic acid components, and a fluorine substitution at the 2'-position of the sugar (Formula I):

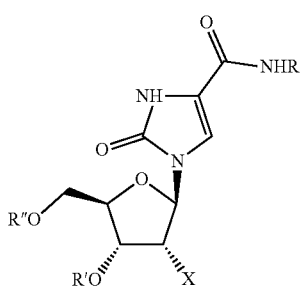

Formula I where
X is H or F;
R is H or a linear or branched $C_{(1-7)}$ alkyloxycarbonyl group;
R' is H; or a hydroxyl protecting group, e.g., an acyl, such as acetyl, butanoyl, benzoyl or amino acyl, such as valyl; R" is H; or a hydroxyl protecting group, e.g., an acyl, such as acetyl, butanoyl, benzoyl or amino acyl, such as valyl; or a phosphate ester, e.g., a 5'-monophosphate, 3',5'-cyclic phosphate, 5'-diphosphate and 5'-triphosphate, or an amino acid alkyl ester phosphoramidate PO(OPh)NHCR'''COOR'''' or phosphorodiamidate PO(NHCR'''COOR'''')$_2$, where R''' is an amino acid side chain and R'''' is a linear or branched $C_{(1-4)}$ alkyl.

As a non-limiting example and not to be bound to any particular theory, the anti-viral properties can be manifested as described below. The fluorine at the 2'-position ribo-configuration of the sugar of Formula I is a close analog of both ribose and 2'-deoxyribose which would target both RNA and DNA viruses.

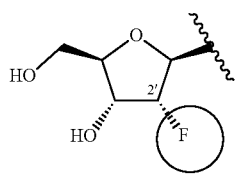 [SMILES: *[C@@H]1O[C@H](CO)[C@@H](O)[C@H]1F]

The 2'-fluoro-substituted analog incorporation into DNA can have a destabilizing effect on the secondary structure of the nucleic acids [19]. This is because the 2'-fluorine-substituted furanose ring adopts an RNA-like 3'-endo (north) pucker that has a strong gauche effect and can affect base-pairing kinetics and thermodynamics [20].

The 2'-F substitution has the additional beneficial effect of protecting against degradation of the free nucleoside metabolite by pyrimidine phosphorylases, such as thymidine and uridine phosphorylase. The presence of the strongly electron withdrawing fluorine prevents glycosyl bond cleavage and keeps the integrity of the nucleoside molecule and prevents the release of the free base and its potential adverse effects in vivo.

The 2'-fluoro substitution in the ribo-configuration of similar nucleoside analogs has previously been disappointing. Ribavirin, a potent anti-HCV drug discussed above, has lost activity upon conversion to its 2'-fluoro derivative [21]. Similarly, a group of 6-heteroaryl-7-deazapurine nucleosides with potent cystostatic and HCV activities did not show significant activity upon 2'-fluoro substitution [22]. $N^4$-hydroxycytidine also lost biological activity upon 2'-F substitution [23].

Substitution of the methyl group of the imidazol-2-one sidechain at the 4-position of imidine with an amino group results in the formation of a carboxamide side chain that is expected to be co-planar with the ring, due to conjugation.

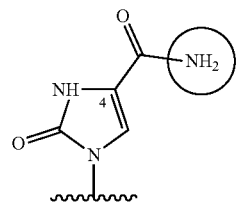 [SMILES: *n1cc(C(N)=O)[nH]c1=O]

Free rotation between 2 predominant conformations and keto-enol tautomerization result in four structural variants (the enol tautomers being energetically less favorable):

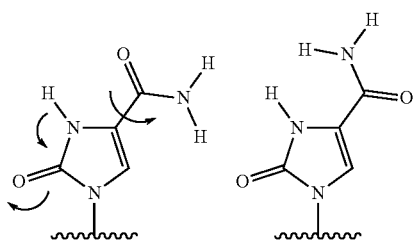

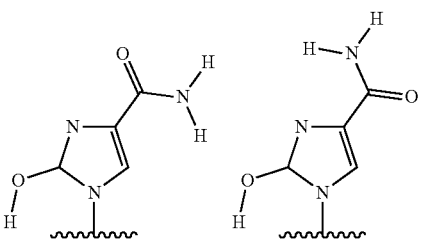

that can cause replication errors, both upon incorporation of the analog, as well as when the incorporated base serves as a template. It is anticipated that preferential base-pairing would occur with both adenine (A) and guanine (G), with one form that resembles uracil (U-like), and one that resembles cytosine (C-like), respectively:

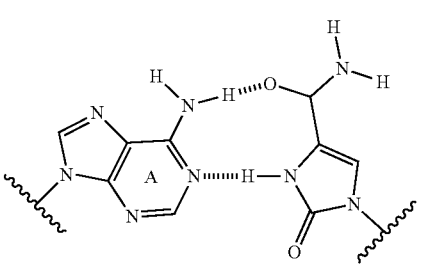

base-pair with A (U-like)

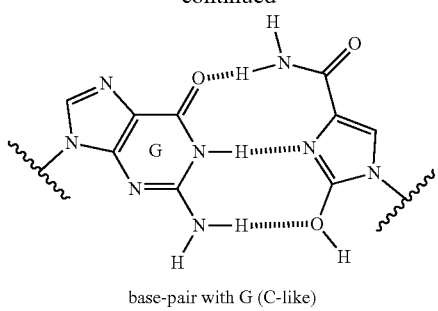

base-pair with G (C-like)

The imidazol-2-one-4-carboxamide base can be considered a "universal base", previously shown to have the following base-pairing preferences: >A>G>T>C [24]. Incorporation into viral DNA can lead to lethal mutagenesis that kills viruses by replication catastrophe [25].

Formula I also has the advantage of not losing biological activity by enzymatic deamination that occurs in molecules such as 2'-deoxy-2'-fluorocytidine (FdCyd), [26], [27], because the amino group is part of the carboxamide side chain and carboxamides are not substrates for nucleoside and nucleotide deaminases.

A bio-reversible alkyloxycarbonyl group attached to the carboxamide sidechain creates carbamate prodrugs with increased lipid solubility and membrane permeability. The resulting carbamate prodrug moiety is susceptible to hydrolysis by carboxylesterases, such as CES1 and CES2, to the otherwise unprotected free nucleoside of Formula I (R'=R"=H) of the present disclosure. Carbamates are hydrolyzed by carboxylesterases slower than esters, because the carbonyl group is less reactive to nucleophilic attack by the active site serine residue of the enzyme, due to the electron-donating effect of the neighboring nitrogen. This permits longer half-life of the carbamate prodrugs than the simple ester prodrugs (Formula I, R'=acyl) in the circulation.

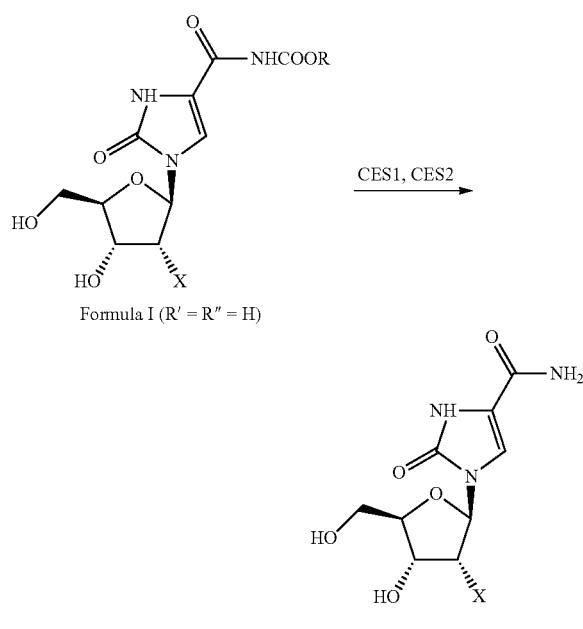

The close structural resemblance of the intracellular free nucleoside form of the Formula I compounds to the natural nucleosides of cytosine and uracil (Cyd, dCyd, Urd and dUrd) renders them to be likely substrates for cellular pyrimidine nucleoside kinases, such as deoxycytidine kinase and uridine-cytidine kinase. These enzymes are necessary for the intracellular metabolic activation of the analogs by phosphorylation to the corresponding 5'-monophosphates. In case this process is inefficient, pronucleotide derivatives known in the art can be made, which deliver the monophosphate into cells, bypassing the kinase step [28]. For example, the structure of amino acid alkyl ester phosphorodiamidate pronucleotide derivatives of compounds of Formula I (R'=H, PN) can be represented as shown below.

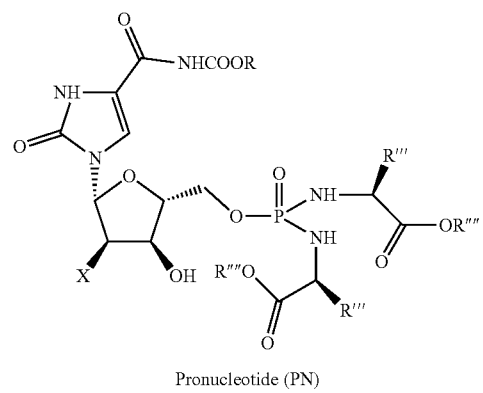

Pronucleotide (PN)

The common intracellular metabolites of compounds of Formula I of the present disclosure responsible for their antiviral activity are the 5'-triphosphate forms. They are expected to be generated in virally infected cells by three consecutive cellular kinase-mediated phosphorylation steps (FIG. 1). Most importantly, the triphosphate metabolites should serve as substrates for viral DNA and RNA polymerases, competing against the natural triphosphates, as well as able to get incorporated into viral nucleic acids. The fact that cellular polymerases have much higher insertion fidelity than viral polymerases, and that in the case of DNA, cells possess effective mismatch repair processes, a significant degree of selectivity for compounds of Formula I of the present disclosure can be predicted. Likewise, in the case of RNA, rare mistakes in individual cellular RNA molecules have little consequence, since they do not have hereditary significance, unlike the viral genomic RNAs.

Metabolic activation of compounds of Formula I of the present disclosure requires the participation of many enzymes (FIG. 1). Systemic prodrug activation will involve removal of the R and R' groups by hydrolytic enzymes to generate the free nucleosides and their pronucleotide derivatives, PN. While the pronucleotides can enter cells by diffusion across the cell membrane, the free nucleosides require the assistance of nucleoside transporters, most likely a member of the equilibrative nucleoside transporters, such as hENT1 (SLC29A1). Inside cells, the free nucleosides and the pronucleotides are converted to the 5'-monophosphates, and further phosphorylated to the corresponding di- and triphosphates. The triphosphates may serve as substrates to viral RNA-dependent RNA polymerases (RdRp), like in the case of HCV and SARS-CoV-2, as well as to DNA- and RNA-dependent DNA polymerases (reverse transcriptases), like in the case of DNA viruses and retroviruses. The incorporated analogs are responsible for miscoding the viral genome and for the detrimental effects on the replication and viability of these viruses.

The emergence of drug resistant microorganisms, including viruses, is inevitable, because antimicrobial drugs select for resistant strains by killing the sensitive ones. Possible resistance against compounds of Formula I of the present disclosure may be expected to emerge as a result of the evolution of structural mutants of the primary viral targets, i.e., the viral DNA or RNA polymerases, which would have lost their affinity to the analog triphosphates. However, considering their close structural similarity to the natural triphosphate substrates and to the existence of multiple active forms of the imidazole-2-one carboxamide base of the analog, it is expected that this would be a relatively rare event.

Figure 2:
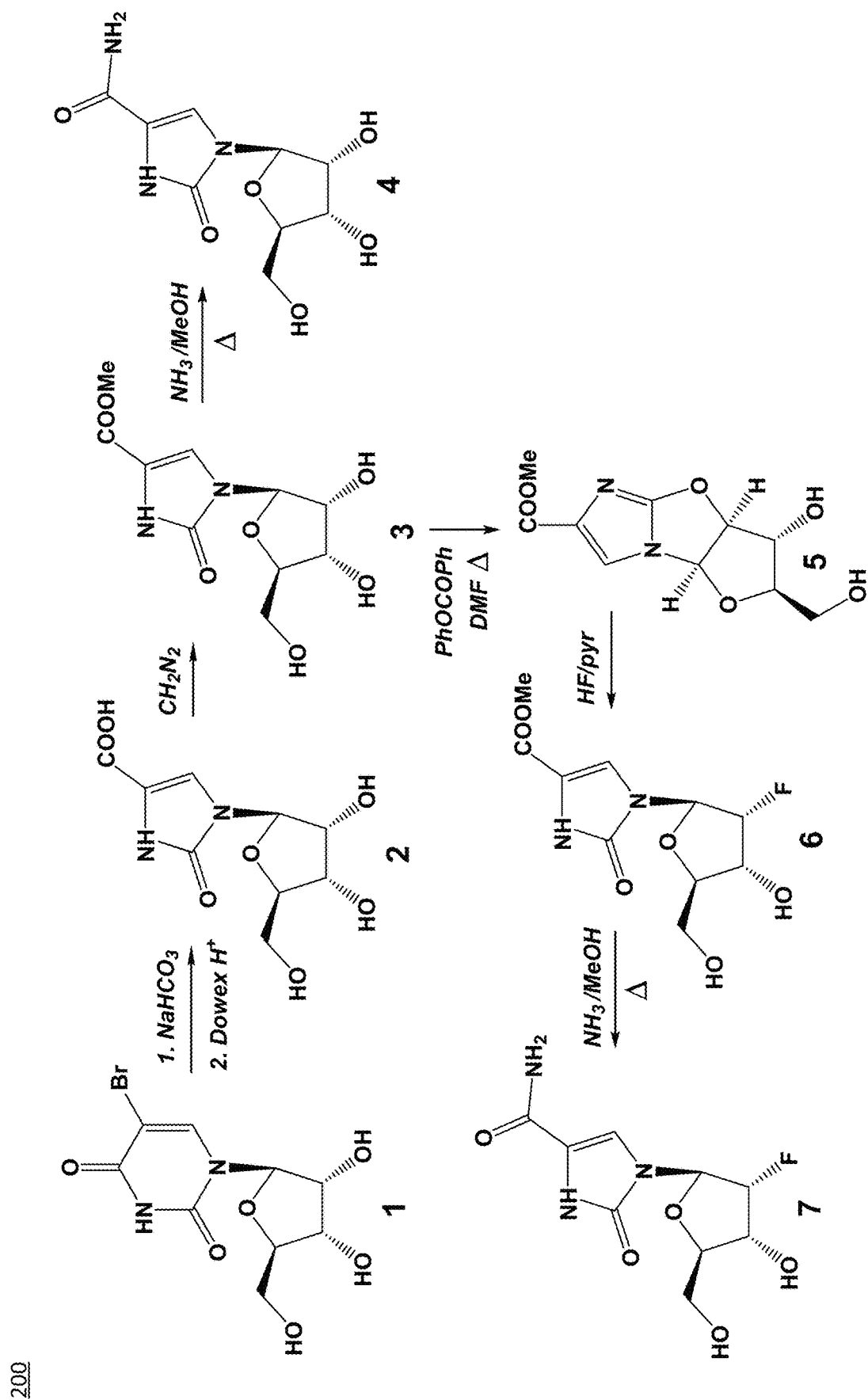
FIG. 2 shows an example outlining the synthesis of the free carboxamide nucleosides 4 and 7 (Formula I (X=H and F; R=R'=R"=H), in accordance with one or more embodiments of the present disclosure.

Compounds of Formula 1 (X=H and F; R=R'=R"=H) can be synthesized as outlined in FIG. 2 using 5-bromouridine (1) as starting material that is readily available commercially. Under basic conditions, 1 can undergo ring contraction to yield carboxylic acid 2, after acidification using Dowex H$^+$ resin [29], which can be converted, without isolation, to the methyl ester 3 using diazomethane. Ammonolysis of methyl ester 3 can yield the free carboxamide nucleoside 4. Intramolecular cyclization of 3 to form the anhydeonucleoside 5 followed by ring opening using HF in pyridine provides 6, the 2'-fluoro derivative of methyl ester 3, that after ammonolysis can yield target compound 7.

Figure 3:
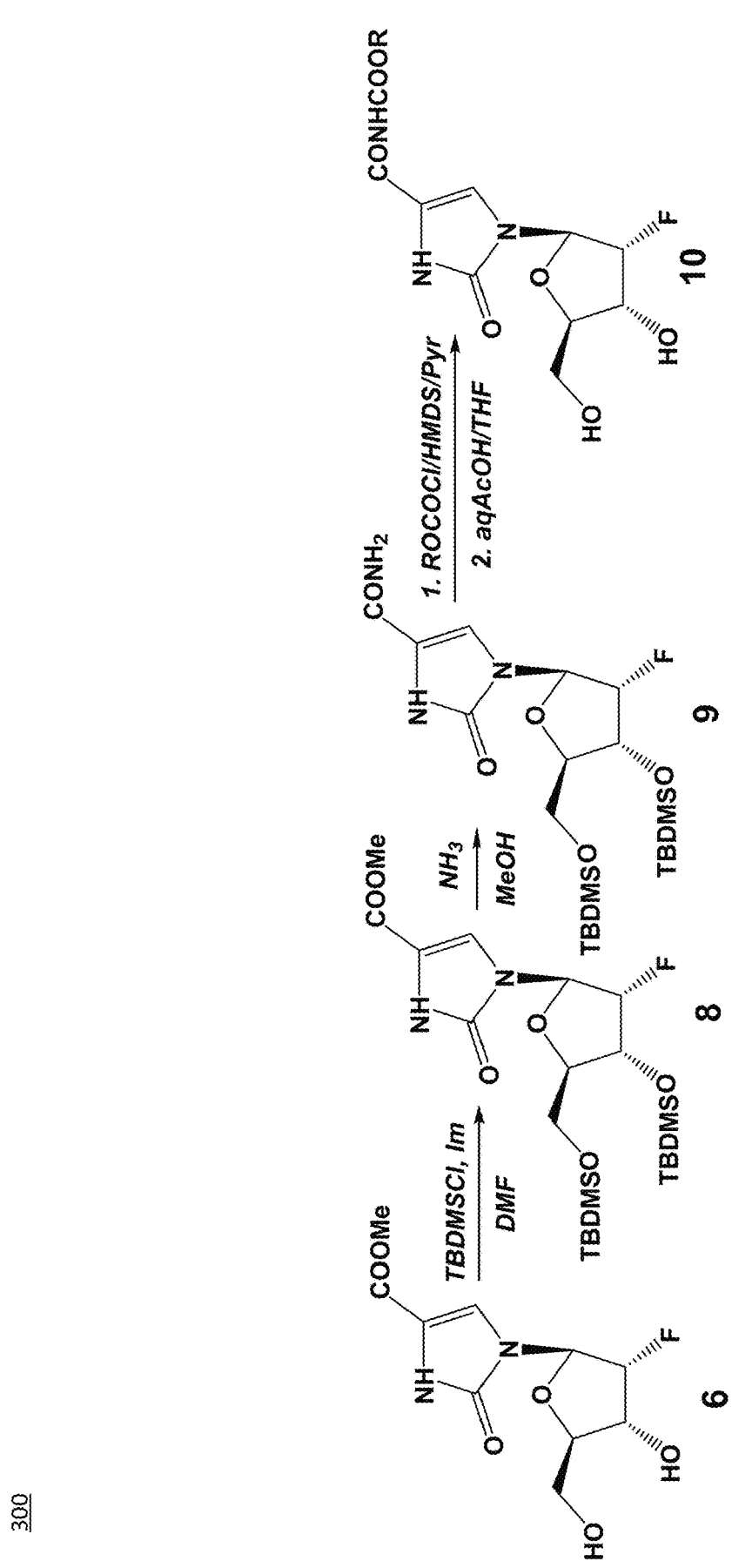
FIG. 3 shows an example outlining the synthesis of the carbamate prodrug derivatives with unprotected sugar moieties (Formula I, X=F; R'=R"=H), in accordance with one or more embodiments of the present disclosure.

Silylation of the sugar hydroxyls of 7 using tert-butyldimethylsilyl chloride (TBDMS-Cl) can yield the silyl-protected nucleoside 8, as outlined in FIG. 3. Ammonolysis of methyl ester sidechain of 8 can yield the carboxamide 9 that can be converted to the carbamate using alkylchloroformate in pyridine. Removal of the silyl groups under acidic conditions can yield the carbamate prodrug 10 (Formula I, X=F; R'=R"=H).

Figure 4:
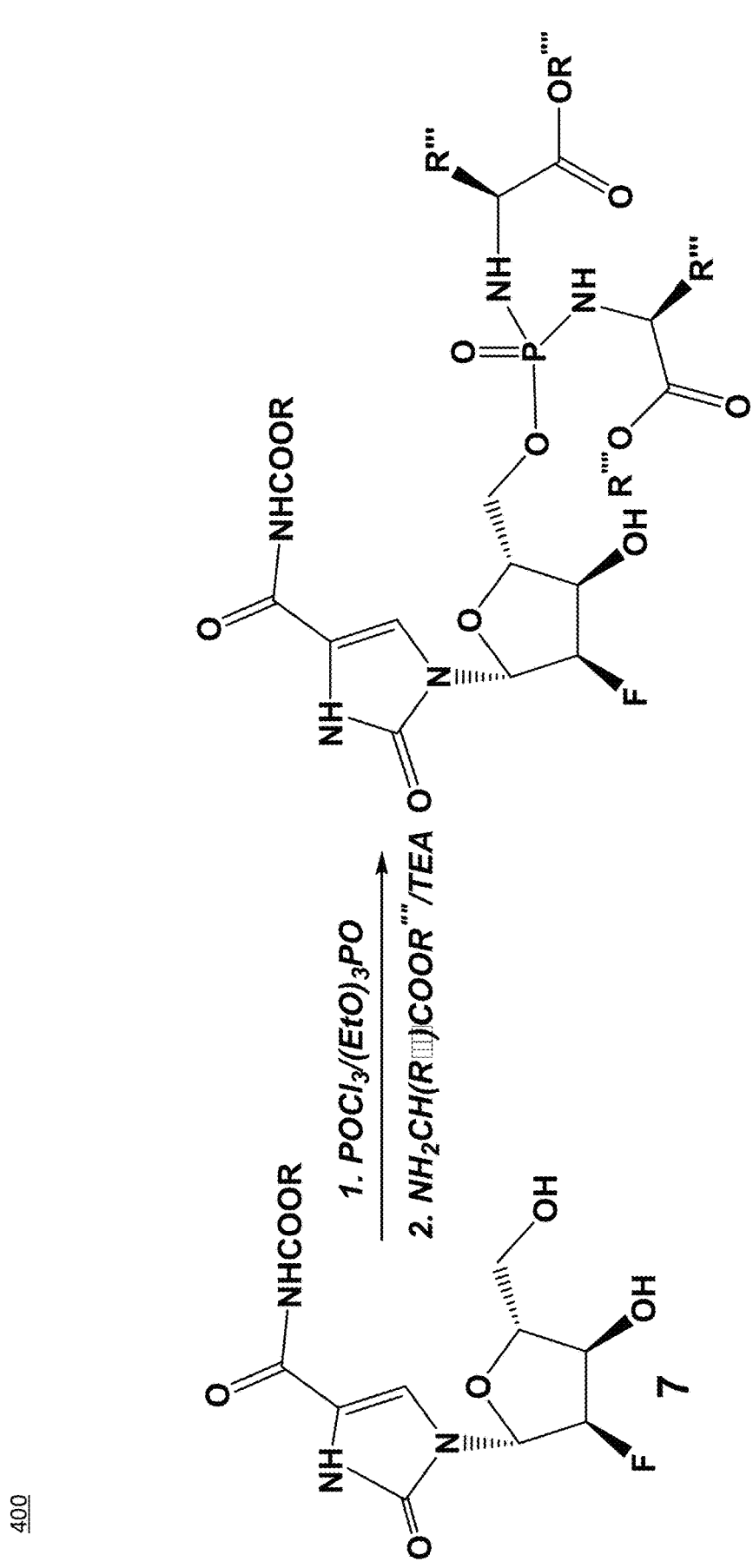
FIG. 4 shows an example outlining the synthesis of the phosphorodiamidate pronucleotide derivatives (Formula I, X=F; R'=H), in accordance with one or more embodiments of the present disclosure.

An example of the 2-step synthesis of the phosphorodiamidate pronucleotides of compounds of Formula I (X=F; R'=H) is shown in FIG. 4.

The present disclosure provides compositions comprising one or more compounds of Formula I and one or more pharmaceutically acceptable salts and carriers. A composition may be formulated in solid or liquid form, including, but not limited to capsules, tablets, powders, aerosols, and solutions made with pharmaceutically-acceptable solvents, suitable for oral, parenteral, and other suitable types of administration.

Compounds disclosed herein may be administered to warm-bodied animals, including humans, alone or in combination with other antiviral agents and/or immune enhancers.

Combinations of different antiviral agents may be required to combat drug resistance that may render individual drugs ineffective. Preferably, but not exclusively, such combinations should be chosen from drugs that act by different mechanisms of action. Since compounds of Formula I exert their effects by interfering with the replication of viruses by interacting with nucleic acid polymerases, the other preferred drugs in the combination should act at by interfering with different aspects of the viral life cycle. Such agents may include, but are not limited to, inhibitors of viral proteases or the synthesis of structural proteins, like spike or matrix proteins or components of the nucleocapsid, and the like.

All the prodrug forms of compounds of Formula I, carbamates, esters, and pronucleotide derivatives were designed for potential in vivo applications. The disclosed compounds are expected to show significant direct-acting antiviral activity in vitro and in vivo. The most preferred carbamate derivatives are N$^4$-pentyloxycarbonyl derivatives. The 5-carbon alkyl group falls into the optimal range of the substrate specificity of the carbamate prodrug activating enzymes CES1 and CES2 [30].

Oral bioavailability may be further improved by protecting the 3'-OH with an appropriate bio-reversible amino acyl group, like valyl, that can also make salt formation possible, like hydrochloride.

REFERENCES

Citations to the following references are provided below, which are referenced throughout the present application for ease of explanation and to provide additional clarity with respect to various concepts. These citations are listed below and referenced in the present application with like bracketed numbers, e.g. [X].

[1] UNAIDS DATA2019, UNAIDS.org 2020.
[2] Jordheim, L P et al. Advances in the development of nucleoside and nucleotide analogues for cancer and viral diseases. *Nature Rev. Drug Discovery*, 2013, 12, 447.
[3] Li, G and De Clercq, E, Therapeutic options for the 2019 novel coronavirus (2019-nCoV). *Nat. Rev. Drug Discovery* 2020, 19, 149.
[4] Loeb, L A et al., Lethal mutagenesis of HIV with mutagenic nucleoside analogs. *Proc. Natl. Acad. Sci.* 1999, 96, 1492.
[5] Kalman, T. I., Ed., Drug action and design: mechanism-based enzyme inhibitors. *Developments in Biochemistry*, Vol. 6. Elsevier/North Holland, N.Y., 1979.
[6] Mathur, P et al., Use of ribavirin for hepatitis C. treatment in the modern direct-acting antiviral era. *J. Clin. Trans. Hepatol.* 2018, 6, 431.
[7] NIH.gov/coronavirus, *ClinicalTrials.gov*, NCT04276688.
[8] Ferron, F et al., Structural and molecular basis of mismatch correction and ribavirin excision from coronavirus RNA. *Proc. Natl. Acad. Sci.* 2018, 115, E162.
[9] Stockman, J L et al, SARS: systematic review of treatment effects. *Plos Med.* 2006, 3, e343.
[10] ClinicalTrials.gov, NCT04359615.
[11] NIH.gov/coronavirus, *ClinicalTrials.gov*, NCT04280705.
[12] Sheahan, T P et al., Broad-spectrum antiviral GS-5734 inhibits both epidemic and zoonotic coronaviruses. *Sci. Transl. Med.* 2017, 9, eaal3653.
[13] Stuyver L J et al., Ribonucleoside analogue that blocks replication of bovine viral diarrhea and hepatitis C viruses in culture. *Antimicrob. Agents Chemother.* 2003, 47, 244.
[14] Sheahan, T P et al., An orally bioavailable broad-spectrum antiviral inhibits SARS-CoV-2 in human airway epithelial cell cultures and multiple coronaviruses in mice. *Sci. Transl. Med.* 2020, 12, eabb5883 *Sci. Transl. Med.* 2020, 12, eabb5883.
[15] Hernandez-Santiago, BI et al., Metabolism of the anti-hepatitis C virus nucleoside β-D-N$^4$-hydroxycytidine in different liver cells. *Antimicrob. Agents Chemother.* 2004, 48, 4636.
[16] Jiang, X-J and Kalman, TI, Synthesis of a novel antiretroviral agent: 1-(2-deoxy-β-D-ribofuranosyl)-4-acetylimidazolin-2-one (imidine). *Nucleosides Nucleotides* 1994, 13, 379.
[17] Kalman, TI, Antiviral imidazolone nucleoside derivatives. WO 199421658A1.
[18] Kalman, TI et al., Mechanism of inhibition of HIV reverse transcriptase by 1-(2'-deoxy-β-D-ribofuranosyl)-4-acetylimidazolin-2-one (imidine). *Nucleosides Nucleotides* 1999, 18, 847.

[19] Ikeda, H et al., The effects of two antipodal fluorene-induced sugar puckers on the conformation and stability of the Dickerson-Drew dodecamer duplex [d(CGCGAAT-TCGCG)]$_2$. *Nucleic Acid Res.* 1998, 26, 2237.

[20] Williams, A A et al., Impact of sugar pucker on base pair and mispair stability, *Biochemistry* 2009, 48, 11994.

[21] Slater, M J et al., Enzymatic synthesis and antiviral activity of 2'-deoxy-2'-fluoro-ribavirin. *Bioorg. Med. Chem. Let.* 1996, 6, 2187.

[22] Perilkova et al., Synthesis of 2'-deoxy-2'-fluororibo- and 2'-deoxy-2',2'-difluororibonucleosides derived from 6-(het)aryl-7-deazapurines, *Tetrahedron* 2012, 68, 8300.

[23] Shi, J. et al., Synthesis and antiviral activity of a series of D- and L-2'-deoxy-2'-fluororibonucleosides in the subgenomic HCV replicon system, *Bioorg. Med. Chem.* 2005, 13, 1641.

[24] Cadena-Amaro, C and Pochet, S, Efficient incorporation of 1-(2-deoxy-β-D-ribofuranosyl)-2-oxo-imidazole-4-carboxamide, *Tetrahedron* 2005, 61, 5081.

[25] Eigen, M, Error catastrophe and antiviral strategy. *Proc. Natl. Acad. Sci.* 2002, 99, 13374.

[26] Doerr, I L and Fox J J, 2'-Deoxy-2'-fluorocytidine, 1-β-D-arabinofuranosyl-2-aminofuranosyl-2-amino-1,4 (2H-4-iminopyrimidine) and related derivatives. *J. Org Chem.* 1967, 32, 1462.

[27] Stuyver, L J et al., Inhibition of subgenomic hepatitis C virus replicon in Huh-7 cells by 2'-deoxy-2'-fluorocytidine. *Antimicrob. Agents Chemother.* 2004, 48, 651.

[28] Wagner, C et al., Pronucleotides: Toward the in vivo delivery of antiviral and anticancer nucleotides. *Med. Chem. Rev.* 2000, 20, 417.

[29] Otter, B A, et al., Nucleosides. LXI. Transformations of pyrimidine nucleosides in alkaline media. IV. Conversion of 5-hydroxyuridines into imidazoline nucleosides. *J. Org. Chem.* 1969, 34, 2626.

[30] Sanghani, S P, Human carboxylesterases: An update on CES1, CES2 and CES3. *Protein Peptide Let.* 2009, 16, 1207.

EXAMPLES

The following examples are presented to illustrate the present disclosure. They are not intended to be limiting in any manner.

Example 1

This example provides a description of the synthesis of methyl 1-(2-deoxy-β-D-ribofuranosyl)-2-oxo-2,3-dihydro-1H-imidazole-4-carboxylate (3.

5-Bromo-2'-fluoro-2'-deoxyuridine (1, 3.5 g, 10 mmol) was dissolved in a 200 mL aqueous solution of NaHCO$_3$ (2.52 g, 30 mmol), and the solution refluxed for 20 h under N$_2$, until no starting material remains by TLC (CHCl$_3$/MeOH/AcOH=6:2:0.5, v/v). The reaction mixture was passed through a column of ion exchanged resin (Dowex 50W X8, 100-200 mesh, H$^+$-form to convert the Na-salt to the free acid 2. This solution of 2 was concentrated under reduced pressure and the residue was dissolved in 100 mL MeOH. To this solution, excess diazomethane in ether was added portion-wise at 4° C. with stirring. The reaction was monitored by TLC (CHCl$_3$/MeOH/AcOH=6:2:0.5, v/v), until all carboxylic acid was consumed. The solvent was removed under reduced pressure and the residue was absorbed on 10 g of silica gel. The product was purified by column chromatography (CH$_2$Cl$_2$/MeOH=20:1, v/v) and crystallized from MeOH to yield 3 as a white powder (1.68 g, 61%). Anal. calcd for C$_{10}$H$_{13}$N$_3$O$_6$: C, 44.28; H, 4.80; N, 15.50. Found: C, 43.96; H, 4.84; N, 15.64.

Example 2

This example provides a description of the synthesis of methyl 1-(2-fluoro-2-deoxy-3,5-di-O-t-butyldimethylsilyl-β-D-ribofuranosyl)-2-oxo-2,3-dihydro-1H-imidazole-4-carboxylate (8).

To a solution of compound 6 (3.9 g, 15 mmol) and imidazole 94.4 g, 66 mmol) in 30 mL of anhydrous DMF, t-butyldimethylsilyl chloride (TBDMS, 4.97 g, 33 mmol) was added. The reaction mixture was stirred for 24 h at room temperature. After removal of the solvent under reduced pressure, the residue was dissolved in 30 mL CHCl$_3$, washed 3× with water and dried over anhydrous Na$_2$SO$_4$. The product crystallized from MeOH/H$_2$O (10:2) to yield 7.5 g of 8 as a white powder (95%). Anal. calcd for C$_{24}$H$_{43}$FN$_2$O$_6$Si$_2$.H$_2$O: C, 48.89; H, 7.59; N, 5.19. Found: C, 48.50; H, 7.68; N, 5.25.

Example 3

This example provides a description of the synthesis of 1-(2-fluoro-2-deoxy-β-D-ribofuranosyl)-2-oxo-2,3-dihydro-1H-imidazole-4-carboxyamide (7).

Compound 6 (516.5 mg, 2 mmol) was dissolved in 15 mL NH$_3$-saturated MeOH and heated in a sealed bomb at 80° C. for 5 days. The solvent was evaporated under reduced pressure and the residue was purified on a silica gel column (CH$_2$Cl$_2$/MeOH=20:1, v/v) to yield 213 mg (75.1%) of the title compound (7). $^1$H NMR (DMSO-d$_6$) δ 6.14 (1H, d, J$_{1'-F}$=16.5 Hz, 1'-H), 5.62 (1H, br s, 3'-OH), 5.15 (1H, m, 5'-OH), 5.35 (1H, dd, J$_{2'-F}$=53 Hz, 2'-H), 4.45 (1H, d, J$_{3'-F}$=23.0 Hz, 3'-H), 4.02 (1H, m, 4'-H), 3.65 (2H, m, 5'-H), 7.30 (1H, s, 5-H), 7.20-7.35 (2H, m, NH$_2$), (1H, bs, NH). $^{13}$C NMR (DMSO-d$_6$) δ 60.10 (5'-C), 68.42 (d, J$_{3'-F}$ 16.2 Hz, 3'-C), 83.75 (4'-C), 85.21 (d, J$_{1'-F}$ 32.5 Hz, 1'-C), 93.46 (d, J$_{2'-F}$186.2 Hz, 2'-C), 112.9 (5-C), 117.7 (4-C), 152.5 (2-C), 160.5 (CONH$_2$). $^{19}$F NMR (DMSO-d$_6$) δ −204.35 (2'-F). Anal. calcd for C$_9$H$_{12}$FN$_3$O$_5$: C, 41.13; H, 4.60; N, 16.09. Found: C, 41.26; H, 4.82; N, 16.12.

Example 4

This example provides a description of a mechanism of the metabolic activation of the sidechain alkyl carbamate prodrug moiety of compounds of Formula I.

Enzymatic hydrolysis catalyzed by carboxylesterases (e.g., CES1) unmasks the free carboxamide via formation of an unstable carboxylate intermediate that decomposes with liberation of CO$_2$ (R"=alkyl):

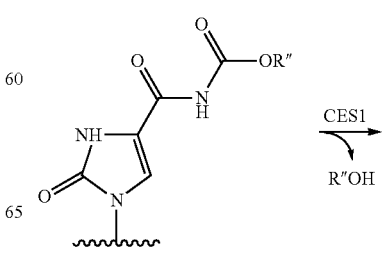

13

-continued

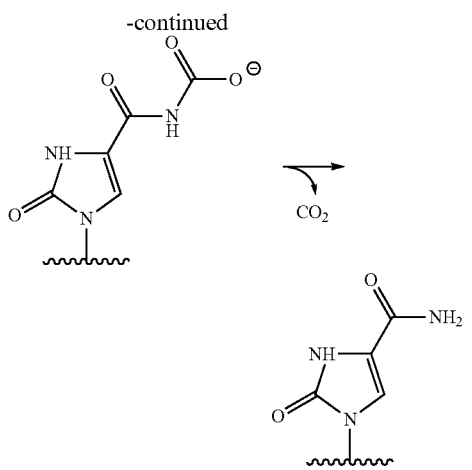

Example 5

This example provides a description of a mechanism of the metabolic activation of the amino acid ester phosphorodiamidate prodrug moiety at the 5'-position of the sugar of compounds of Formula I. Intracellular esterase hydrolysis of the amino acid ester moiety of a pronucleotide (PN), followed by intramolecular cyclization leads to a cyclic phosphoester intermediate that collapses into a monophosphoramidate. Further hydrolysis by the phosphoramidase activity of histidine triad nucleotide-binding protein 1 (HINT1), a regulatory molecule, results in the formation of the 5'-monophosphate:

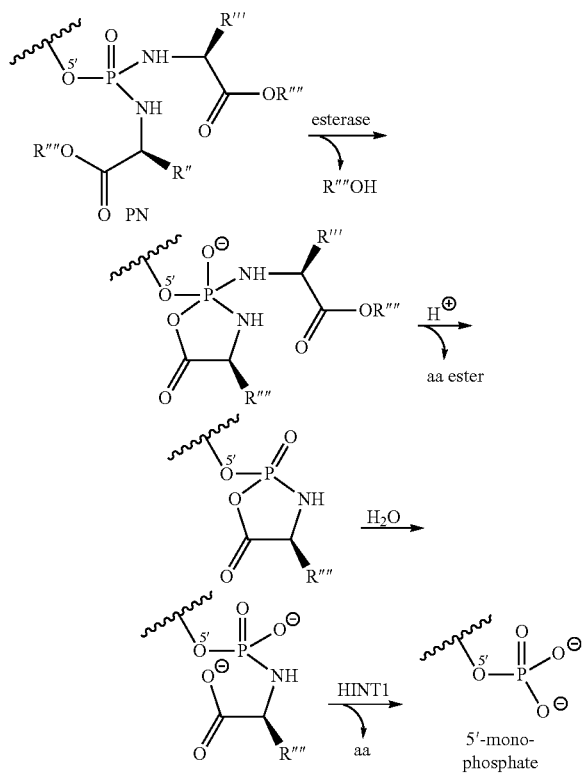

14

What is claimed is:
1. A compound of the formula:

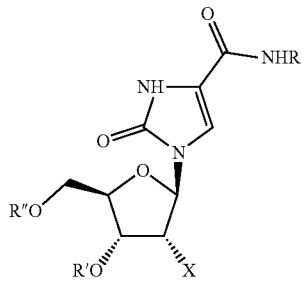

wherein:
X is F;
R is H or a linear or branched $C_{(1-7)}$ alkyloxycarbonyl group;
R' is H or a hydroxyl protecting group;
R" is H, a hydroxy protecting group, or a phosphate ester, phosphoramidate or phosphorodiamidate;
and pharmaceutically acceptable salts thereof.

2. The compound of claim 1, wherein the alkoxycarbonyl group is pentyloxycarbonyl.

3. The compound of claim 1, wherein the hydroxyl protecting group is an acyl or amino acyl.

4. The compound of claim 1, wherein the phosphate ester is a 5'-monophosphate, 3',5'-cyclic phosphate, 5'-diphosphate or 5'-triphosphate.

5. The compound of claim 1, wherein the phosphoramidate is an amino acid alkyl ester phosphoramidate PO(OPh)NHCR'''COOR'''', where R''' is an amino acid side chain and R'''' is a linear or branched $C_{(1-4)}$ alkyl.

6. The compound of claim 1, wherein the phosphorodiamidate is an amino acid alkyl ester phosphorodiamidate is PO(NHCR'''COOR '''')$_2$, where R''' is an amino acid side chain and R'''' is a linear or branched $C_{(1-4)}$ alkyl.

7. The compound of claim 1, wherein the hydroxyl protecting group is an acetyl, butanoyl, benzoyl, or valyl.

8. The compound of claim 1, wherein the hydroxyl protecting group is an acetyl, butanoyl, or benzoyl.

9. The compound of claim 3, wherein the hydroxyl protecting group is a valyl.

10. A composition comprising the compound of claim 1, and a pharmaceutically acceptable carrier.

11. The composition of claim 10, wherein the composition further comprises one or more antiviral drugs.

12. A method of treating an individual having a viral infection comprising administering to the individual the composition of claim 10, wherein administering the composition results in reduction or elimination of the viral infection in the individual.

13. A method of treating an individual having a viral infection comprising administering to an individual the composition of claim 10, wherein administering the composition results in prevention of a viral infection in the individual.

14. The method of claim 12, wherein said viral infection is caused by a coronavirus, a flavivirus, hepatitis, herpes, immunodeficiency, or an influenza virus.

15. The method of claim 12, wherein the individual is a human or non-human mammal.

16. The method of claim 12, wherein viral RNA or DNA replication is inhibited.

17. The method of claim 14, wherein the method induces analog misincorporation into viral RNA or viral DNA, resulting in the death of a virus.
18. The method of claim 12, wherein the composition comprises at least one compound having the following structure:
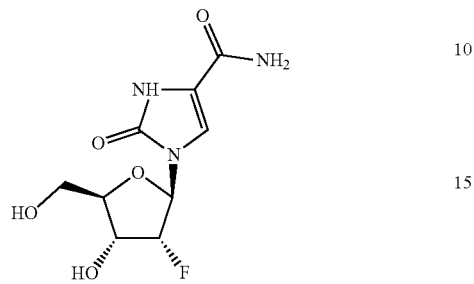
1-((2R,3R,4R,5R)-3-fluoro-4-hydroxy-5-(hydroxymethyl)tetrahydrofuran-2-yl)-2-oxo-2,3-dihydro-1H-imidazole-4-carboxamide.
* * * * *